US00PP12404P2

(12) United States Plant Patent
Zimmermann

(10) Patent No.: US PP12,404 P2
(45) Date of Patent: Feb. 12, 2002

(54) HOP PLANT NAMED YCR ACCESSION NO. 5

(75) Inventor: Charles E. Zimmermann, Prosser, WA (US)

(73) Assignee: Yakima Chief Ranches, Inc., Sunnyvale, CA (US)

( * ) Notice: Subject to any disclaimer, the term of this patent is extended or adjusted under 35 U.S.C. 154(b) by 0 days.

(21) Appl. No.: 09/287,405

(22) Filed: Apr. 6, 1999

(51) Int. Cl.[7] ..... A01H 5/00

(52) U.S. Cl. ..... Plt./236
(58) Field of Search ..... Plt./236

*Primary Examiner*—Bruce R. Campell
*Assistant Examiner*—Anne Marie Grünberg
(74) *Attorney, Agent, or Firm*—Straton Ballew PLLC

(57) ABSTRACT

A new hop plant variety is disclosed. The variety is a cultivar of recent origin, used for its bittering and aromatic properties. The new variety is moderately tolerant to powdery mildew and Sphaerotheca. The new variety produces a medium size cone with good pickability and storageability. The cones mature relatively late, and crop yield is 2750 to 3000 pounds per acre (3080 to 3360 kg/ha).

8 Drawing Sheets

BACKGROUND AND SUMMARY OF INVENTION

This invention relates to a new and distinct variety of hop plant, and more particularly to a new hop plant variety of unknown parentage which was discovered among plants created as part of a controlled breeding program. The new variety has been stably reproduced over successive generations. Discovery of the new variety and initial reproduction by root cuttings was carried out in a research nursery in Prosser, Wash., U.S.A. Subsequent asexual reproduction took place in Granger, Wash., U.S.A.

THE DRAWINGS

DESCRIPTION OF THE VARIETY

Figure 1:
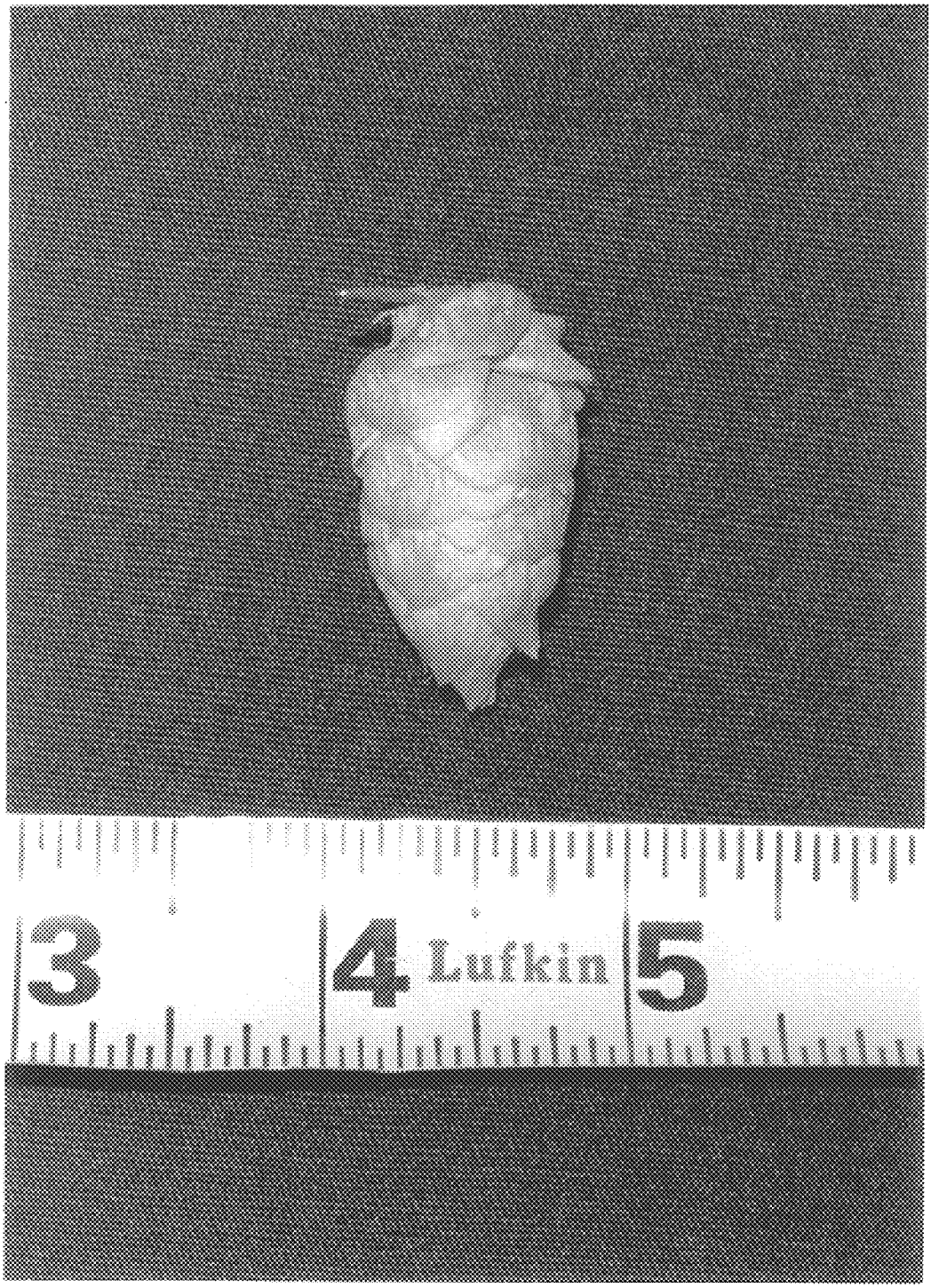
FIG. 1 shows a hop cone of the new hop plant variety.
Figure 2:
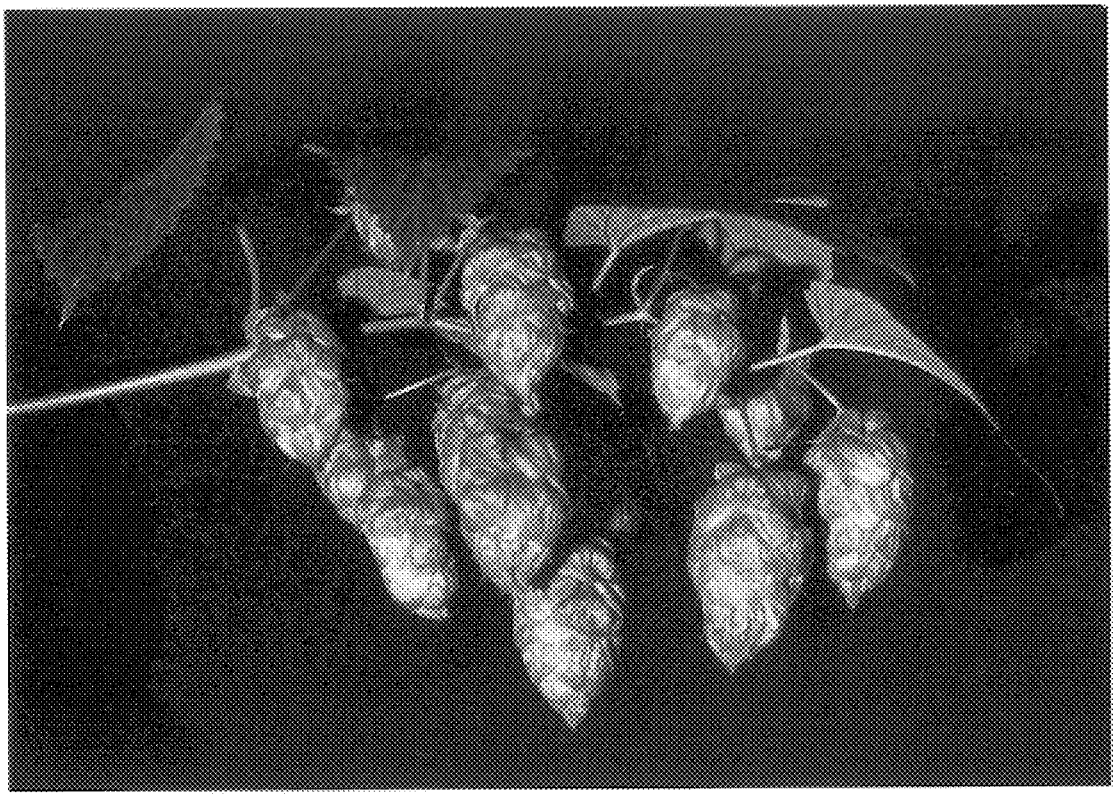
FIG. 2 shows a cluster of hop cones of the new hop variety.
Figure 3:
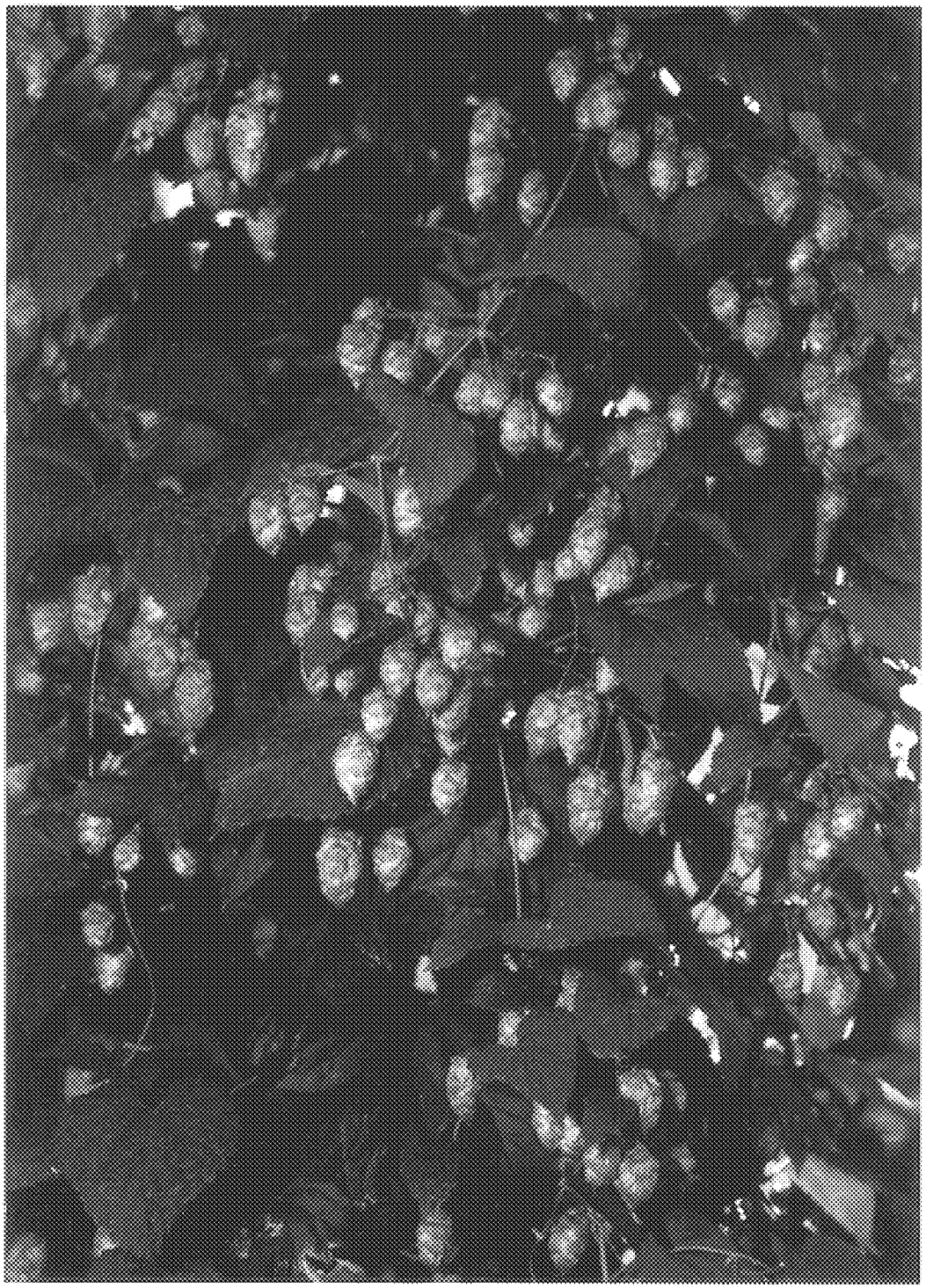
FIG. 3 shows hop cones of the new hop variety.
Figure 4:
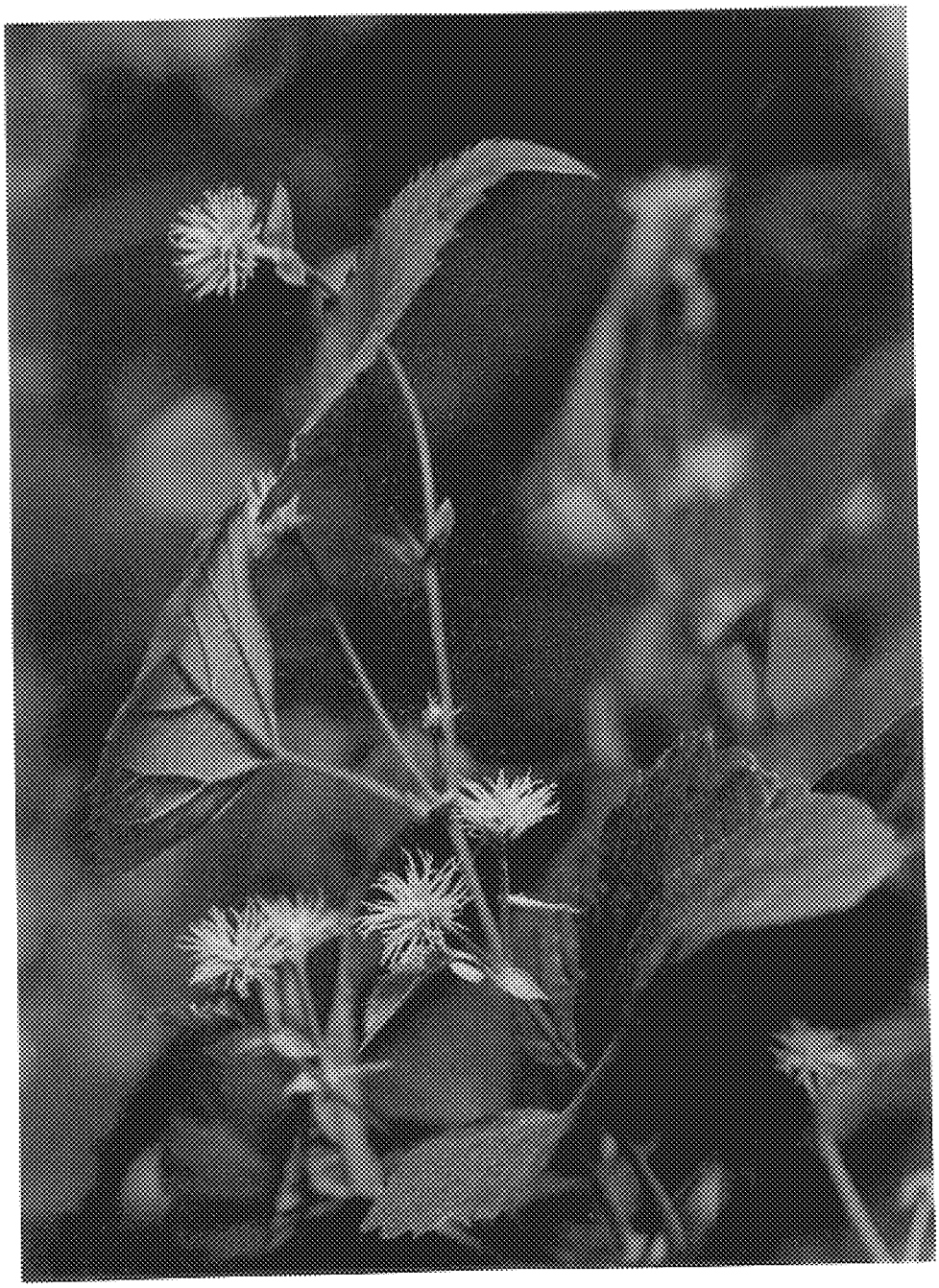
FIG. 4 shows a blossom and leaf of the new hop plant variety.
Figure 5:
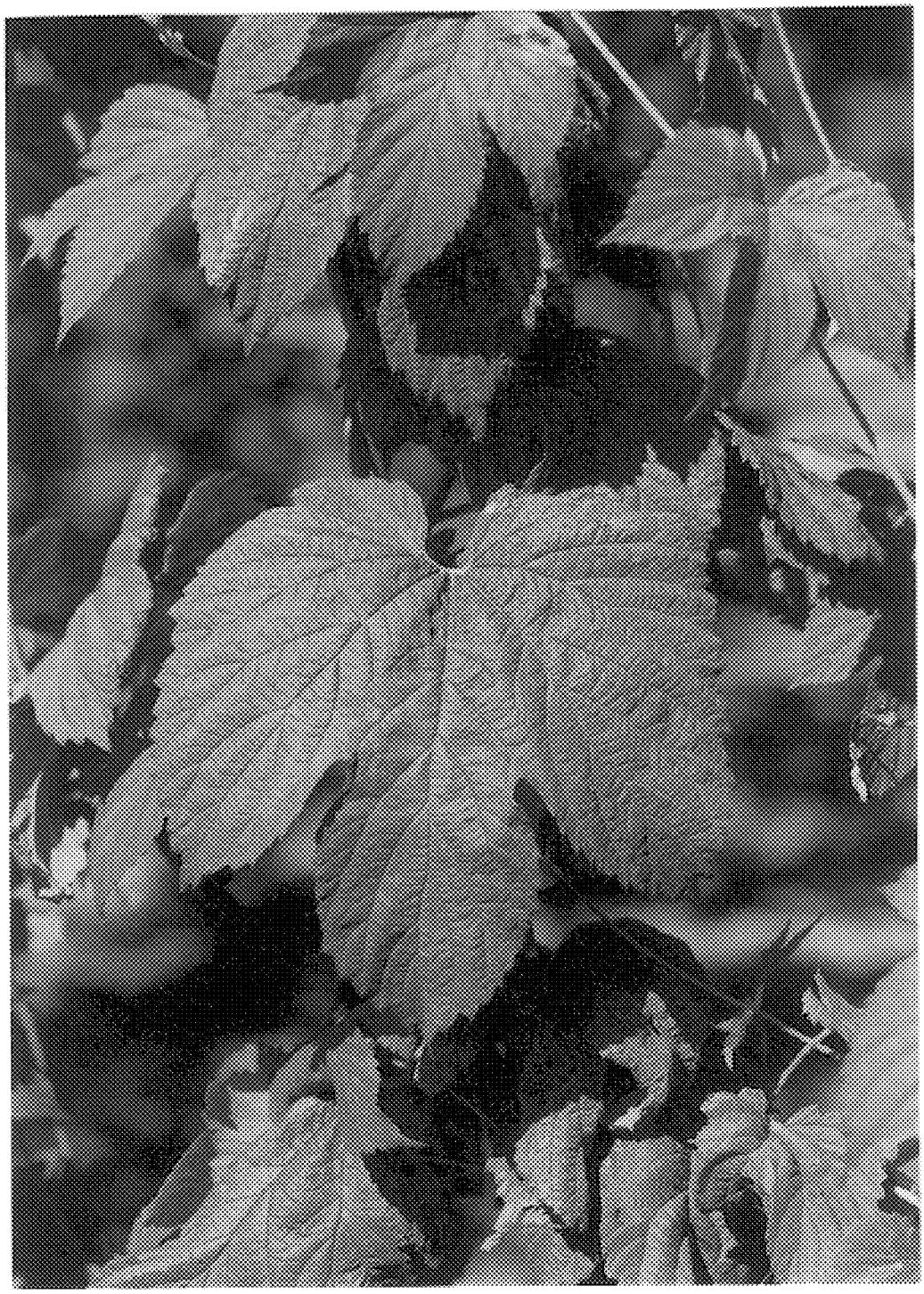
FIG. 5 shows a leaf on the new hop plant variety.
Figure 6:
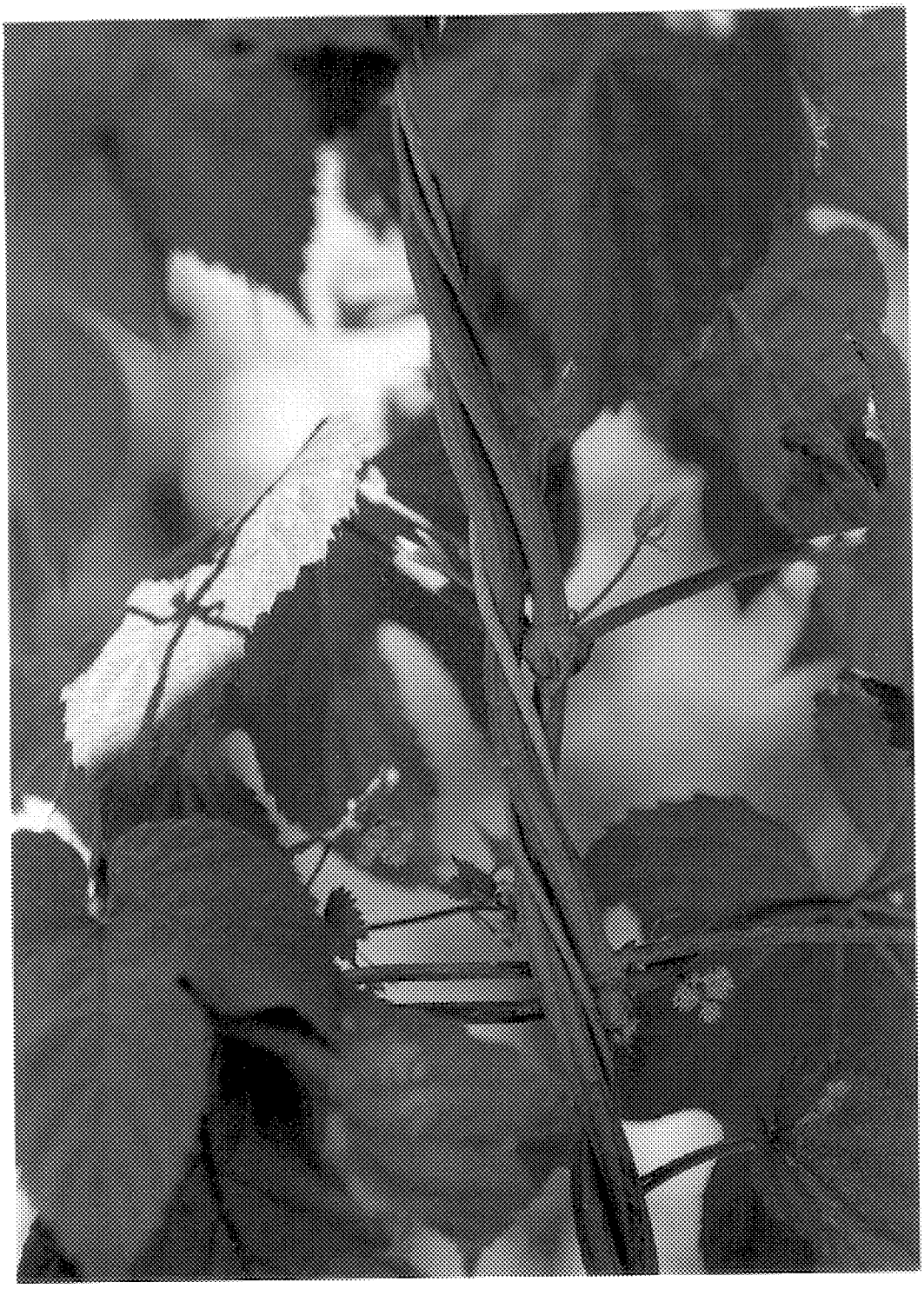
FIG. 6 shows a bine of the new hop plant variety.
Figure 7:
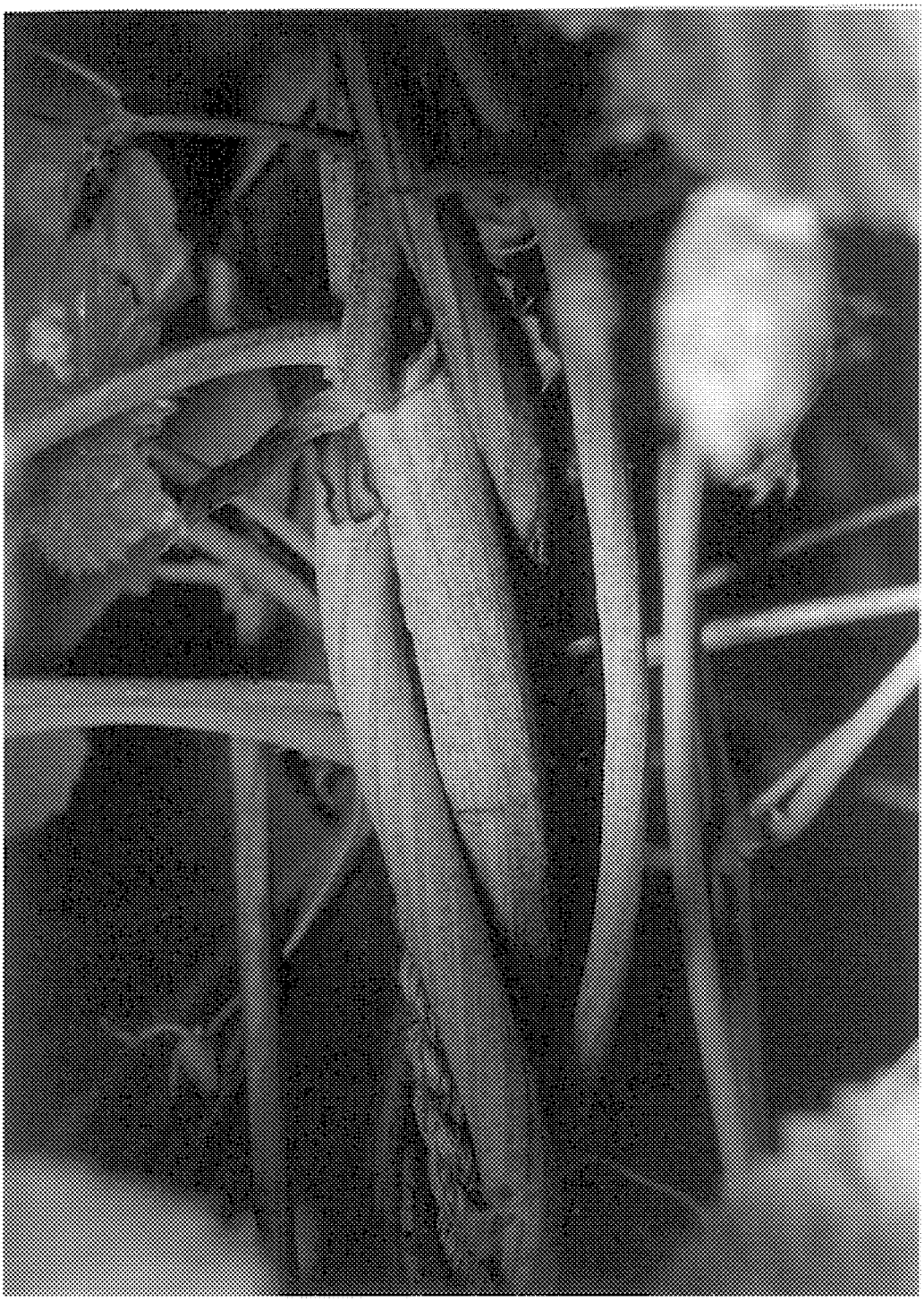
FIG. 7 shows a bine of the new hop plant variety.
Figure 8:
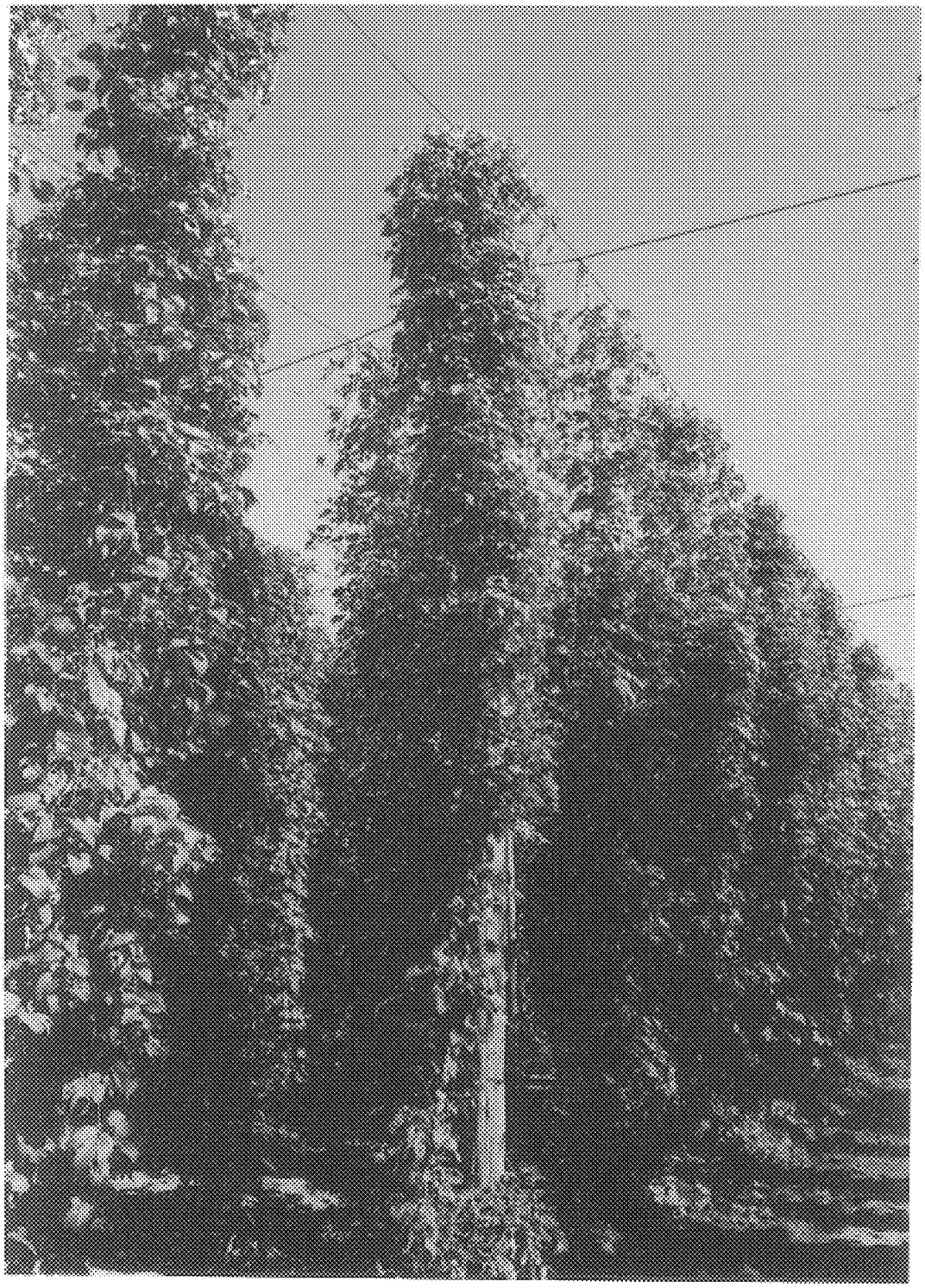
FIG. 8 shows a hop plant of the new variety.

The new hop plant variety is a cultivar of recent origin, used for its bittering and aromatic properties. The new variety is moderately tolerant to powdery mildew and Sphaerotheca. The new variety produces a medium size cone with good pickability (similar to Nugget, unpatented) and storageability (18% to 20% alpha loss after 6 months common storage). The cones mature relatively late (after Sep. 15 in Granger, Wash., and crop yield is 2750 to 3000 pounds per acre (3080 to 3360 kg/ha).

The following is a detailed botanical description of the new and distinct variety of *Humulus lupulus*, based on observations of specimens grown in Granger, Wash. during the 1998 growing season. All colors are described according to The Royal Horticultural Society Colour Chart. It should be understood that the botanical and analytical chemical characteristics described will vary somewhat depending upon cultural pactices and climatic conditions and can vary with location and season.

1. Bine:
   - *Color*.—Yellow green (146D).
   - *Stripe*.—Greyed purple (183C).
   - *Stipule color*.—Light green (146B 146C).
   - *Stipule direction*.—Up.
   - *Diameter*.—1.0 cm (measurement taken at 2.75 m).
   - *Shoot emergence*.—Late; similar to Nugget.
2. Leaves:
   - *Leaf arrangement*.—Opposite.
   - *Leaf shape*.—Cordate to palmate.
   - *Average length*.—20.2 cm.
   - *Average width*.—20.1 cm.
   - *Color — upper surface, mature*.—Yellow green (147A).
   - *Color — lower surface, mature*.—Green (137C).
   - *Color — upper surface, immature*.—Green (137A).
   - *Color — lower surface, immature*.—Green (146A).
   - *Number of leaf lobes*.—1–5.
   - *Margin*.—Serrate.
   - *Serrations per inch*.—3 min., 5 max.
   - *Pose*.—Downward.
   - *Average petiole length*.—7.4 cm.
   - *Petiole color at base*.—Greyed purple (183C).
   - *Venation*.—Palmate.
3. Cones
   - *Average length*.—3.2 cm.
   - *Average diameter*.—1.6 cm.
   - *Color*.—Bract tip: Yellow green (144A). Bract base: Yellow green (145C). Bracteole: Yellow green (145C).
   - *Shape*.—Conic.
   - *Bract shape*.—Ovate.
   - *Bract tip shape*.—Acute.
   - *Bract tip position*.—Recurved.
   - *Bracteole shape*.—Ovate.
   - *Shattering potential at harvest*.—Medium to medium-high; Similar to Cluster.

% *Alpha acids*.—15.0%–17.0% of cone weight (ASBC Spectrophotometric method).

% *Beta acids*.—4.5%–5.5% of cone weight (ASBC Spectrophotometric method).

% *Cohumulone*.—24.0%–26.0% of alpha acids.

*Total oils*.—1.0–2.0 mL/100 g.

*Aroma*.—Mild, citrus with piney notes.

4. Technical data: Essential Oil Profile of YCR Accession No. 5: 112 mg of 10% Adsorbate/150C/5 Min. by DTD-GC-MS.

| MS Spec # | Area Integration | Peak Assignment | Area % |
|---|---|---|---|
| 55–213 | 27156 | acetone + isoprene + trace of dimethylsulfide | 0.460 |
| 227–292 | 15055 | 2-methyl-3-buten-1-ol | 0.255 |
| 351 | 2363 | acetic acid | 0.040 |
| 361 | 1044 | methylpentanone | 0.018 |
| 372 | 1194 | ? m/z 56, 70 peaks | 0.020 |
| 402 | 808 | 3-methyl-2-butenal | 0.014 |
| 414 | 460 | hexanal | 0.008 |
| 425 | 1558 | isobutyric acid | 0.026 |
| 430 | 1318 | n-octane | 0.022 |
| 483 | 5004 | 3-methylbutyric acid | 0.085 |
| 489 | 1531 | 2-methylbutyric acid | 0.026 |
| 507 | 566 | 2-methyl-2-butanol acetate | 0.010 |
| 521 | 6875 | ? m/z 82/81/67 peaks | 0.116 |
| 526 | 3067 | 2,6-dimethyl-2,4-heptadiene + methyl ester of unsat. fatty acid | 0.052 |
| 534 | 3429 | 5,5-dimethyl-2(5H)-furanone | 0.058 |
| 543 | 1105 | alpha-pinene | 0.019 |
| 552 | 170 | propylisobutyrate | 0.003 |
| 556 | 604 | 4-methylpentanoic acid | 0.010 |
| 566 | 7373 | 2-methylbutylpropanoate | 0.125 |
| 575 | 154 | 6-methyl-5-heptene-2-one | 0.003 |
| 579 | 15126 | beta-pinene + hexanoic acid | 0.256 |
| 592 | 1149118 | myrcene | 19.472 |
| 596 | 2969 | isobutyl-2-methylbutyrate | 0.050 |
| 604 | 14748 | 3-methylbutylisobutyrate | 0.250 |
| 608 | 29136 | 2-methylbutylisobutyrate | 0.494 |
| 612 | 15786 | methylheptanoate | 0.267 |
| 615 | 307 | alpha-terpinene | 0.005 |
| 618 | 647 | p-cymene | 0.011 |
| 626 | 10479 | limonene + beta-phellandrene | 0.178 |
| 631 | 318 | ? terpene | 0.005 |
| 641 | 16482 | beta-ocimene + pentyl-2-methylpropanoate | 0.279 |
| 653 | 332 | gamma-terpinene | 0.006 |
| 659 | 1394 | isooctanol | 0.024 |
| 669 | 5961 | heptanoic acid | 0.101 |
| 673 | 13282 | methyl-6-methylheptanoate | 0.225 |
| 679 | 759 | linalool oxide + terpinolene | 0.013 |
| 688 | 34689 | linalool + nonanal | 0.588 |
| 694 | 5119 | 2-methylbutyl-2-methylbutyrate | 0.087 |
| 697 | 6371 | pentyl-3-methylbutyrate | 0.108 |
| 704 | 369 | ? sulfur-containing compd. | 0.006 |
| 710 | 36928 | methyloctanoate | 0.626 |
| 722 | 1670 | 2,3-dihydro-3,5-dihydroxy-6-methyl-4(H)-pyran-4-one | 0.028 |
| 731 | 3204 | octanoic acid (branched isomer) | 0.054 |
| 739 | 2549 | hexylisobutyrate | 0.043 |
| 748 | 119 | cis-3-hexenylisobutyrate | 0.002 |
| 760 | 508 | octanoic acid | 0.009 |
| 771 | 35739 | ? 130 m.w. branched alcohol m/z 59 base peak | 0.606 |
| 778 | 2177 | 4,8-dimethyl-1,7-nonadiene | 0.037 |
| 783 | 2014 | 2-decanone | 0.034 |
| 788 | 2362 | methyl-4-octenoate | 0.040 |
| 799 | 7125 | 2-decanol | 0.121 |
| 807 | 2241 | methylnonenoate | 0.038 |
| 815 | 487 | ? 164 m.w. w/149 base peak (phenolic ?) | 0.008 |
| 823 | 19878 | methylnonanoate | 0.337 |
| 829 | 605 | nerol | 0.010 |
| 835 | 174 | ? | 0.003 |

-continued

| MS Spec # | Area Integration | Peak Assignment | Area % |
|---|---|---|---|
| 842 | 211 | 2-methylheptylpropanoate | 0.004 |
| 853 | 1192 | heptylbutyrate | 0.020 |
| 857 | 36749 | geraniol + 2-undecanone (branched isomer) | 0.623 |
| 869 | 345 | methyl-2-methylnonenoate | 0.006 |
| 878 | 3149 | 2-undecanol (branched isomer) | 0.053 |
| 882 | 8038 | nonanoic acid | 0.136 |
| 894 | 8369 | undecenyl alcohol | 0.142 |
| 905 | 50462 | methyldecanoate (branched isomer) + 2-undecanone | 0.855 |
| 911 | 356 | ? | 0.006 |
| 922 | 42630 | 2-undecanol | 0.722 |
| 926 | 423469 | methyl-4-decenoate + methyl-4,8-decadienoate | 7.176 |
| 941 | 13718 | methylgeranate | 0.232 |
| 947 | 41983 | methyldecanoate | 0.711 |
| 977 | 3099 | octyl-2-methylpropanoate | 0.053 |
| 983 | 194 | ? unsaturated alcohol or aldehyde | 0.003 |
| 992 | 4651 | methyl-2-undecenoate | 0.079 |
| 1000 | 4471 | alpha-cubebene | 0.076 |
| 1006 | 1557 | decanoic acid | 0.026 |
| 1016 | 1543 | geranyl acetate | 0.026 |
| 1024 | 469 | ? acetate | 0.008 |
| 1029 | 3764 | alpha-ylangene | 0.064 |
| 1035 | 15885 | alpha-copaene | 0.269 |
| 1040 | 314 | methylundecenoate | 0.005 |
| 1050 | 2284 | ? 204 m.w. sesquiterpene | 0.039 |
| 1054 | 319 | ? | 0.005 |
| 1058 | 678 | ? 204 m.w. sesquiterpene | 0.011 |
| 1073 | 1382 | ? sesquiterpene 206 m.w. 163 base peak | 0.023 |
| 1081 | 327 | methylundecanoate | 0.006 |
| 1094 | 1310323 | caryophyllene | 22.204 |
| 1102 | 26956 | beta-cubebene | 0.457 |
| 1107 | 248 | linalylisobutyrate | 0.004 |
| 1113 | 333 | 3-methylbutyloctanoate | 0.006 |
| 1123 | 1129 | ? 204 m.w. sesquiterpene | 0.019 |
| 1138 | 1860954 | humulene | 31.534 |
| 1143 | 5515 | ? 204 m.w. sesquiterpene 161 base peak | 0.093 |
| 1159 | 57015 | gamma-cadinene | 0.966 |
| 1163 | 3545 | gamma-muuroline | 0.060 |
| 1173 | 72413 | beta-selinene | 1.227 |
| 1180 | 12060 | alpha-amorphene | 0.204 |
| 1186 | 95684 | alpha-selinene | 1.621 |
| 1197 | 3050 | delta-cadinene | 0.052 |
| 1205 | 47521 | alpha-muurolene | 0.805 |
| 1209 | 2391 | calamenene | 0.041 |
| 1216 | 76149 | beta-cadinene | 1.290 |
| 1228 | 6676 | delta-selinene | 0.113 |
| 1235 | 11325 | sesquiterpene w/no common name CAS#16728-99-7, cadinene-type | 0.192 |
| 1245 | 3020 | selina-3,7-diene (eudesma-3,7-diene) | 0.051 |
| 1261 | 1561 | germacrene B or patchoulene | 0.026 |
| 1272 | 437 | caryophyllyl alcohol | 0.007 |
| 1285 | 24922 | caryophyllene oxide | 0.422 |
| 1303 | 2938 | humulene epoxide | 0.050 |
| 1308 | 440 | methyltridecenoate | 0.007 |
| 1317 | 32095 | humulene epoxide | 0.544 |
| 1323 | 1479 | globulol | 0.025 |
| 1328 | 2913 | delta-cadinol | 0.049 |
| 1334 | 238 | ? | 0.004 |
| 1338 | 122 | ? | 0.002 |
| 1343 | 12459 | cadinol isomer | 0.211 |
| 1355 | 12157 | cadinol | 0.206 |
| 1371 | 16917 | alpha-cadinol + Juniper Camphor (eudesma-7-en-4-ol) | 0.287 |
| 1391 | 906 | eudesmol | 0.015 |
| 1443 | 528 | caryophyllyl acetate | 0.009 |
| 1524 | 1363 | ? 250 m.w. w/115 base peak | 0.023 |
| | 5901396 | Total Essential Oil Components | 100.000 |

I claim:

1. A new variety of hop plant substantially as herein shown and described.

* * * * *

UNITED STATES PATENT AND TRADEMARK OFFICE

CERTIFICATE OF CORRECTION

PATENT NO. : PP 12,404 P2
DATED : February 12, 2002
INVENTOR(S) : Charles E. Zimmermann It is certified that error appears in the above-identified patent and that said Letters Patent is hereby corrected as shown below:

Title page,
Item [73], Assignee, replace "Sunnyvale, CA" with -- Sunnyside, WA --.

Signed and Sealed this

Seventeenth Day of September, 2002

*Attest:*

*Attesting Officer*

JAMES E. ROGAN
*Director of the United States Patent and Trademark Office*